(12) United States Patent
Chen et al.

(10) Patent No.: US 9,865,047 B1
(45) Date of Patent: Jan. 9, 2018

(54) SYSTEMS AND METHODS FOR EFFECTIVE PATTERN WAFER SURFACE MEASUREMENT AND ANALYSIS USING INTERFEROMETRY TOOL

(71) Applicant: KLA-Tencor Corporation, Milpitas, CA (US)

(72) Inventors: Haiguang Chen, Mountain View, CA (US); Jaydeep Sinha, Livermore, CA (US); Enrique Chavez, Tracy, CA (US); Sathish Veeraraghavan, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 245 days.

(21) Appl. No.: 14/883,927

(22) Filed: Oct. 15, 2015

Related U.S. Application Data

(60) Provisional application No. 62/069,312, filed on Oct. 28, 2014.

(51) Int. Cl.
| | |
|---|---|
| *G06K 9/00* | (2006.01) |
| *G06T 7/00* | (2017.01) |
| *G06K 9/52* | (2006.01) |
| *G06K 9/62* | (2006.01) |
| *G06K 9/46* | (2006.01) |
| *G06T 5/00* | (2006.01) |

(52) U.S. Cl.
CPC ............ *G06T 7/001* (2013.01); *G06K 9/4642* (2013.01); *G06K 9/52* (2013.01); *G06K 9/6201* (2013.01); *G06K 9/6215* (2013.01); *G06T 5/006* (2013.01); *G06K 2009/4666* (2013.01); *G06T 2207/30148* (2013.01)

(58) Field of Classification Search
CPC ................ G01N 21/9501; G01B 11/06; G01B 11/2441; G06T 2207/30148
See application file for complete search history.

(56) References Cited

U.S. PATENT DOCUMENTS

| | | | |
|---|---|---|---|
| 8,643,847 B1 * | 2/2014 | Chen .................... | G01B 9/0203 356/511 |
| 9,121,684 B2 * | 9/2015 | Tang .................. | G01B 9/02076 |
| 9,632,038 B2 * | 4/2017 | Chen .................. | G01B 11/2441 |
| 2013/0209926 A1 * | 8/2013 | Oshemkov ............ | G03F 7/2002 430/5 |
| 2015/0298282 A1 * | 10/2015 | Vukkadala ............ | B24B 37/005 451/8 |
| 2016/0071260 A1 * | 3/2016 | Azordegan ............ | G01B 11/24 716/123 |

(Continued)

OTHER PUBLICATIONS

U.S. Appl. No. 14/520,998, filed Oct. 22, 2014, Azordegan et al.

(Continued)

*Primary Examiner* — Wesley Tucker
(74) *Attorney, Agent, or Firm* — Suiter Swantz pc llo

(57) ABSTRACT

Systems and methods for providing improved wafer geometry measurements are disclosed. A wafer geometry measurement system may utilize techniques that enable the wafer geometry measurement system to identify and reduce wafer surface errors caused by structures such as patterns on the wafers being measured. The wafer geometry measurement system may also utilize techniques that enable the wafer geometry measurement system to accurately reconstruct patterned wafer surfaces.

29 Claims, 9 Drawing Sheets

(56) References Cited

U.S. PATENT DOCUMENTS

2016/0163033 A1* 6/2016 Vukkadala .............. G06T 7/001
                                                          382/145
2016/0321799 A1* 11/2016 Chen .................. G01B 11/2441

OTHER PUBLICATIONS

U.S. Appl. No. 14/808,994, filed Jul. 24, 2015, Chen et al.
U.S. Appl. No. 14/730,997, filed Jun. 4, 2015, Vukkadala et al.
U.S. Appl. No. 14/313,733, filed Jun. 24, 2014, Vukkadala et al.

* cited by examiner

SYSTEMS AND METHODS FOR EFFECTIVE PATTERN WAFER SURFACE MEASUREMENT AND ANALYSIS USING INTERFEROMETRY TOOL

CROSS-REFERENCE TO RELATED APPLICATIONS

The present application claims the benefit under 35 U.S.C. §119(e) of U.S. Provisional Application Ser. No. 62/069,312, filed Oct. 28, 2014. Said U.S. Provisional Application Ser. No. 62/069,312 is hereby incorporated by reference in its entirety.

TECHNICAL FIELD

The disclosure generally relates to the field of semiconductor fabrication, and particularly to patterned wafer geometry measurement techniques.

BACKGROUND

Thin polished plates such as silicon wafers and the like are a very important part of modern technology. A wafer, for instance, may refer to a thin slice of semiconductor material used in the fabrication of integrated circuits and other devices. Other examples of thin polished plates may include magnetic disc substrates, gauge blocks and the like. While the technique described here refers mainly to wafers, it is to be understood that the technique also is applicable to other types of polished plates as well. The term wafer and the term thin polished plate may be used interchangeably in the present disclosure.

Fabricating semiconductor devices typically includes processing wafers using a number of fabrication processes. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etching, deposition, and ion implantation. Multiple semiconductor devices may be fabricated in an arrangement on a single semiconductor wafer and then separated into individual semiconductor devices.

Metrology processes are used at various steps during a semiconductor manufacturing process to monitor and control one or more semiconductor layer processes. Some of these characteristics include the shape, flatness and thickness uniformity of the wafers. While conventional metrology systems may be able to monitor and control these characteristics, they are generally utilized for handling unpatterned/bare wafers. Therein lies a need for systems and methods for wafer geometry measurements suitable for any wafers, including patterned wafers, without the aforementioned shortcomings.

SUMMARY

An embodiment of the present disclosure is directed to a system. The system may include at least one imaging device configured to acquire at least one of an image of a front surface of a wafer and at least one image of a back surface of the wafer. The system may also include at least one processor in communication with the at least one imaging device. The at least one processor may be configured to: calculate at least one of a front surface phase map of wafer based on the image of the front surface of the wafer and a back surface phase map of the wafer based on the image of the back surface of the wafer; calculate at least one of a front surface height map based on the front surface phase map and a back surface height map based on the back surface phase map of the wafer; identify at least one artifact region within the front surface height map at least partially based on the front surface height map and the back surface height map; generate a reference height map based on the front surface height map with the at least one artifact region excluded; calculate a surface height correction value at least partially based on the reference height map, the front surface height map, and the front surface phase map; and apply the surface height correction value to obtain an error-corrected front surface height map.

A further embodiment of the present disclosure is also directed to a method. The method may include: acquiring a front surface phase map of a wafer; calculating a front surface height map based on the front surface phase map; filtering the front surface height map; identifying at least one region within the front surface height map that contains large height variations; performing convex hull analysis of the front surface height map based on the at least one region to identify at least one artifact region; generating a reference height map based on the front surface height map with the at least one artifact region excluded; calculating a surface height correction value at least partially based on the reference height map, the front surface height map, and the front surface phase map; and applying the surface height correction value to obtain an error-corrected front surface height map.

An additional embodiment of the present disclosure is directed to a method. The method may include: acquiring a front surface phase map of wafer and a back surface phase map of the wafer; calculating a front surface height map based on the front surface phase map and a back surface height map based on the back surface phase map of the wafer; calculating wafer thickness data based on the front surface height map and the back surface height map; identifying at least one artifact region within the front surface height map based on the wafer thickness data; generating a reference height map based on the front surface height map with the at least one artifact region excluded; calculating a surface height correction value at least partially based on the reference height map, the front surface height map, and the front surface phase map; and applying the surface height correction value to obtain an error-corrected front surface height map.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Embodiments of the present disclosure are directed to systems and methods for providing improved wafer geometry measurements. It is noted that the term wafer geometry in the present disclosure refers to wafer front side height, backside height, thickness variation, flatness, and all consequent derivatives such as shape, topography, or the like.

Interferometer wafer metrology systems, such as WaferSight metrology system from KLA-Tencor, may scan both the front and back surfaces of a wafer at the same time. By combining wafer shape, edge roll-off, thickness or flatness, and topography measurements in a single scan, such wafer metrology tools may provide complete data sets that are necessary for topography and wafer geometry monitoring in wafer manufacturing.

It is noted, however, if a wafer being measured has a patterned surface, the phase map of that patterned surface can be very complex to unwrap and the patterned structures on the wafer surface may introduce surface errors that affect measurement accuracies. It is therefore important to design measurement systems and methods that can identify and reduce these types of surface errors in order to accurately reconstruct patterned wafer surfaces. It is contemplated that such measurement systems and methods may also be utilized to monitor and control various wafer fabrication processes with improved accuracy.

Figure 1:
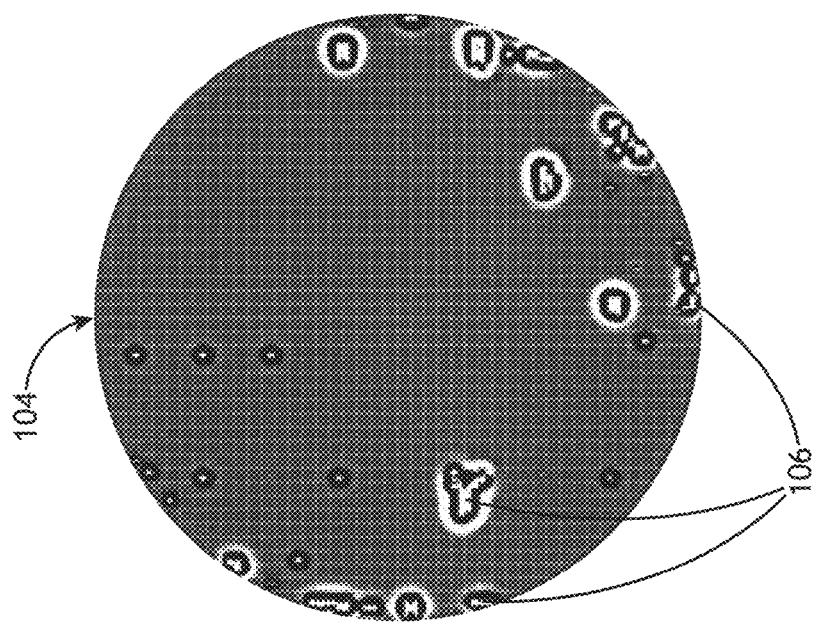
FIG. 1 is an illustration depicting surface errors that are typically observed during patterned wafer geometry measurements.
Figure 1:
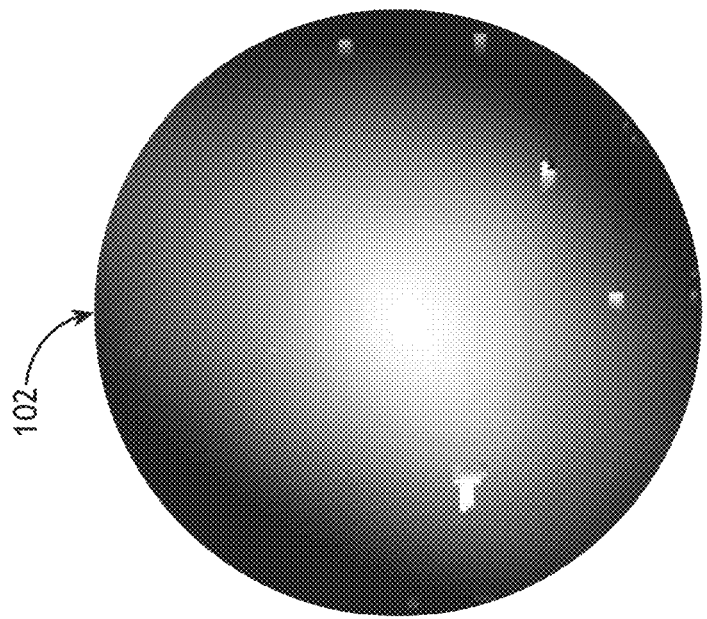

FIG. 1 is an illustration depicting some surface errors that are typically observed during patterned wafer geometry measurements. More specifically, the map 102 depicts a reconstructed patterned wafer surface map (unwrapped from the phase map) and the map 104 depicts the result of processing the map 102 using high-pass filtering. It is noted that there are many erroneous surface bumps 106 (e.g., due to phase unwrapping errors or the like), which may severely affect the accuracy of the measurement.

Figure 2:
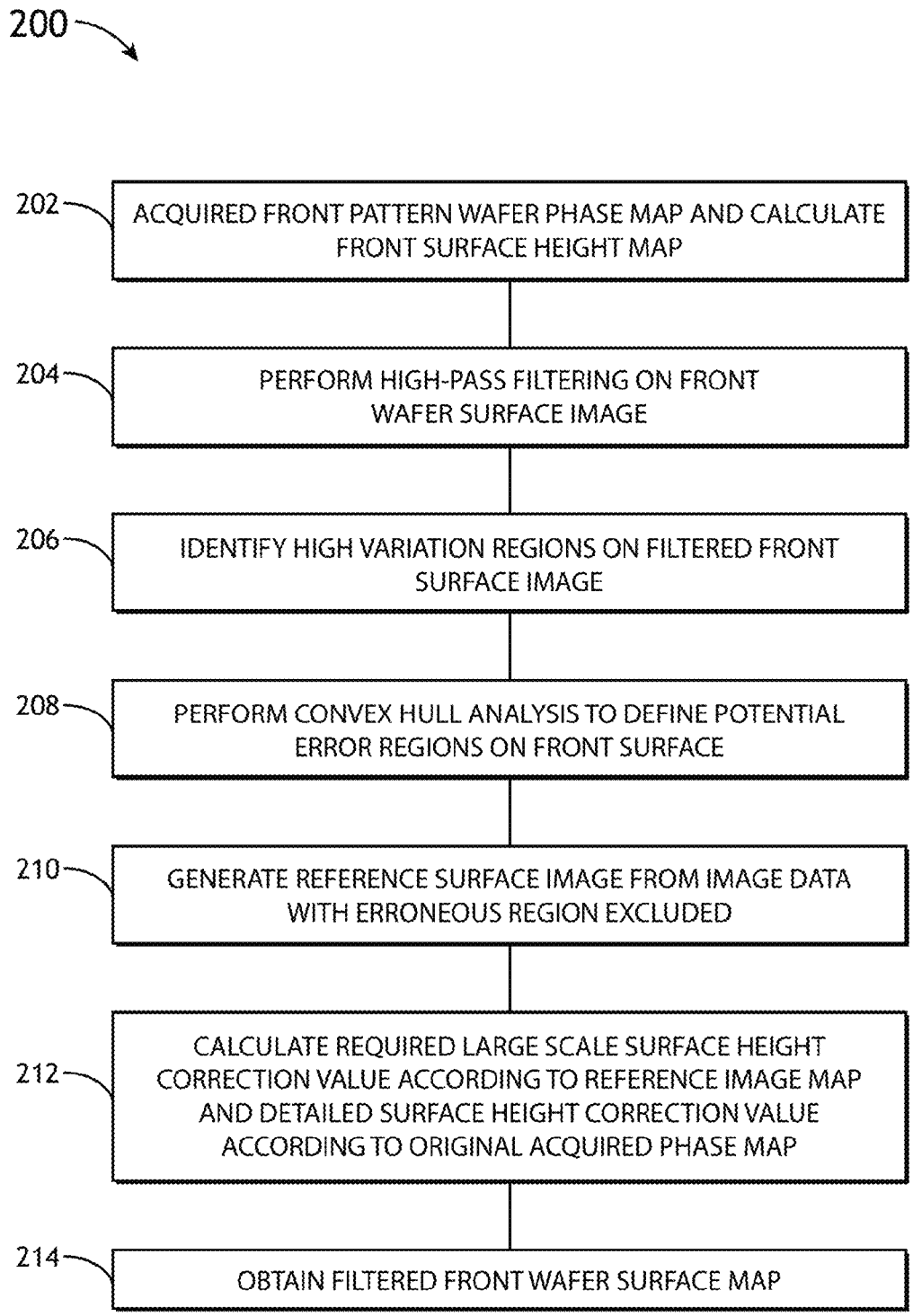
FIG. 2 is a flow diagram depicting an embodiment of a method for identifying surface errors based on surface filtering and convex hull analysis.

The measurement systems and methods disclosed herein may overcome the aforementioned problems by reducing surface errors while still keeping the important wafer shape and pattern structure information intact. FIG. 2 is a flow diagram depicting one of the techniques that may be utilized by the measurement systems and methods disclosed herein.

More specifically, the method 200 may be utilized to accurately identify surface errors based on surface filtering and convex hull analysis. As shown in FIG. 2, the method 200 may first acquire a phase map of the patterned wafer surface from interferometer intensity frames and calculate a surface height map based on the acquired phase map in step 202. Typically, the patterned wafer surface is referred to as the "front" surface while the unpatterned/bare surface is referred to as the "back" surface. It is to be understood, however, that the terms "front" and "back" are merely used to distinguish a first surface of the wafer from a second (opposite) surface of the same wafer. In some instances, the front surface of the wafer may be patterned and the back surface of the wafer may be unpatterned. It is contemplated, however, that such a configuration is merely exemplary and is not meant to be limiting.

Once the surface height map of the front wafer surface is calculated, step 204 may perform filtering (e.g., high-pass filtering) on the front surface height map and step 206 may identify regions of the surface height map that may contain large height variations. For instance, if the surface height variation of a particular region is greater than a surface height variation threshold, that particular region may be considered as an erroneous region due to its large surface height variation. It is contemplated that the surface height variation threshold may be determined manually and/or systematically. For example, in certain implementations, the threshold may be determined at least partially based on the surface slope and/or the wavelength of the laser used by the measurement system. Alternatively and/or additionally, the threshold may be determined based on measurement statistics or some preconfigured settings.

Figure 3:
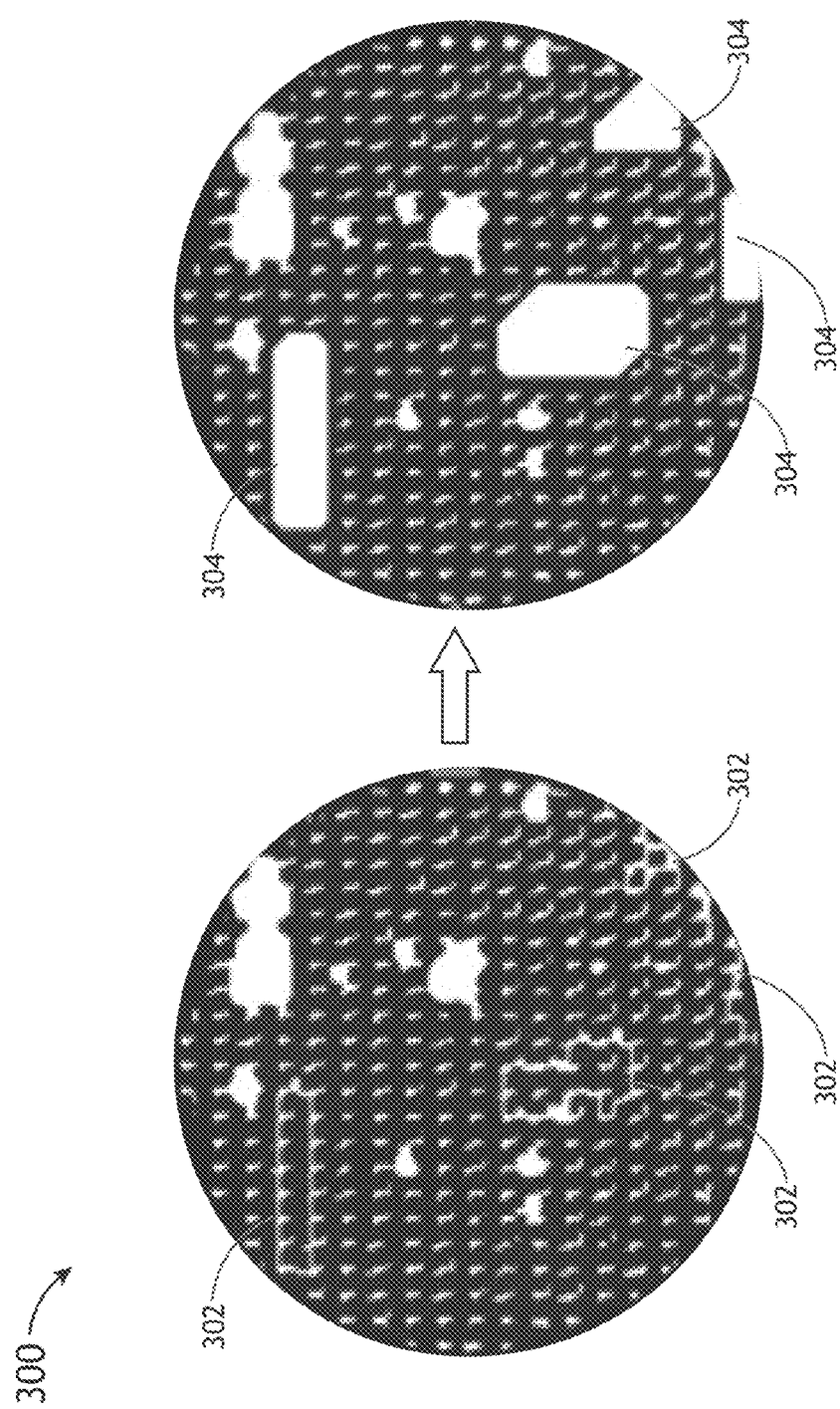
FIG. 3 is an illustration depicting identification of artifact regions.

Once the regions with large surface height variations have been identified, step 208 may be utilized to perform convex hull analysis to identify additional regions that may also be considered erroneous. FIG. 3 is an illustration depicting a convex hull analysis performed on an exemplary wafer 300. It is noted that the convex hull analysis may recognize not only the regions with large surface height variations previously identified in step 206, but also additional regions 304 that are enclosed by the some of the regions 302 already identified in step 206. These additional regions 304, recognized in step 208, may also be considered as erroneous regions along with the regions already identified in step 206.

For illustrative purpose, the erroneous regions identified in steps 206 and 208 may be collectively referred to as artifact regions (shown as white pixels in FIG. 3). Once the artifact regions have been recognized, they may be excluded from the front surface height map so that only artifact-free regions may remain (shown as black pixels in FIG. 3). Step 210 may then fit a polynomial of a selected order (e.g., a two-dimensional polynomial) to the front surface height map containing only the artifact-free regions to generate a reference height map. Subsequently, the difference between the reference height map and the original surface height map can be calculated and used to estimate a large scale surface height correction value in step 212.

In certain implementations, the large scale surface height correction value may be defined as integer multiples of $\lambda/2$ where $\lambda$ is the wavelength of the laser used by the wafer geometry measurement system. For example, if the difference between the reference height map and the original surface height map is $12.2*(\lambda/2)$, the large scale surface height correction may be determined to be $12*(\lambda/2)$.

Figure 4:
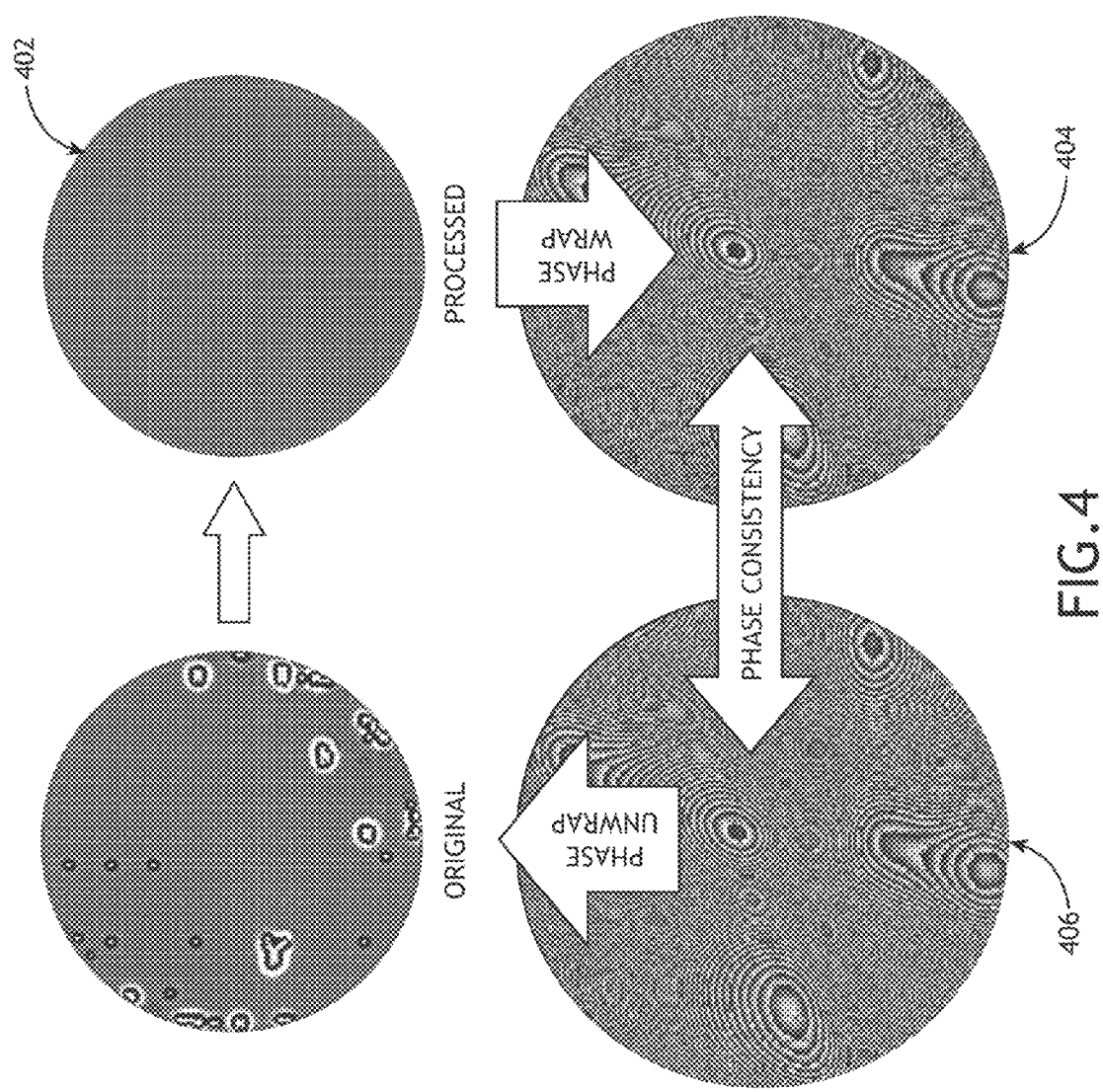
FIG. 4 is an illustration depicting correction of surface errors and phase consistency constraints.

Also calculated in step 212 are the detailed surface height correction values that may be applied to the previously excluded artifact regions (i.e., the white pixels in FIG. 3). The detailed scale surface height correction values may be defined (and illustrated in FIG. 4) as the remaining surface height corrections needed after applying the large scale surface height correction in order to correct the wafer surface height map so that the final corrected wafer surface height map 402 (obtained in step 214) can be remapped (wrapped) into a phase map 404 that is substantially identical to the phase map 406 originally acquired from interferometer intensity frames.

In certain implementations, the artifact-free regions (shown as black pixels in FIG. 3) may be used to help determine the detailed surface height correction values needed for the artifact regions (shown as white pixels in FIG. 3). It is noted that the detailed corrections are only carried out on the artifact regions; no detailed adjustments are needed for the artifact-free regions after the large scale surface height correction. It is noted that performing the correction in this manner allows the correction method 200 to keep the phase maps 404 and 406 consistent while still preserving the wafer surface details. It is also noted that since the correction method 200 is applicable by obtaining only one side of the wafer (e.g., the front surface), the correction method 200 may be appreciated in various applications, especially if the wafer measurement system does not support simultaneous measurements of both sides of the wafer.

Figure 5:
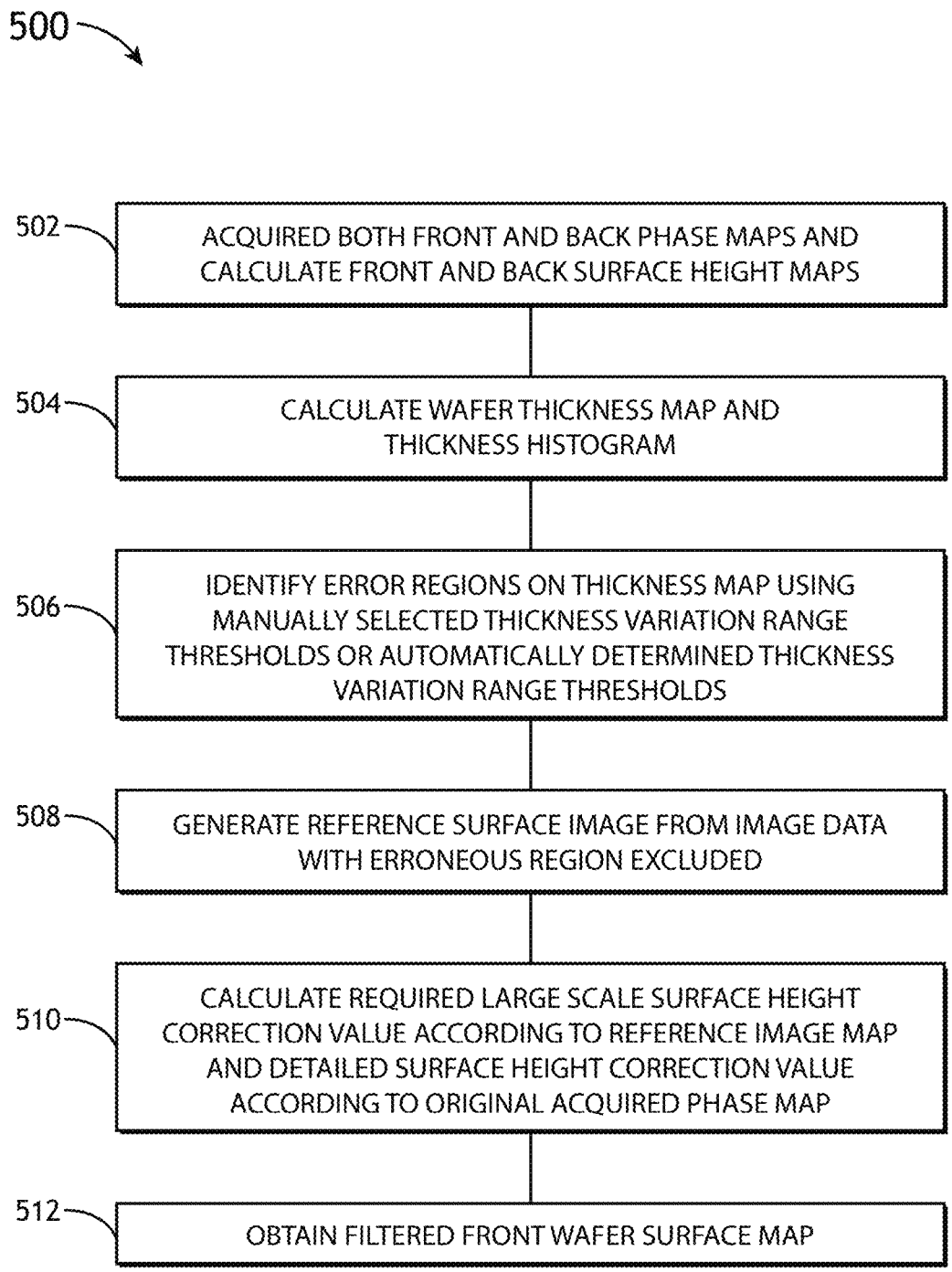
FIG. 5 is a flow diagram depicting an embodiment of a method for identifying surface errors based on wafer thickness.

It is noted, however, that here are measurement systems available that are capable of acquiring wafer front and back surfaces simultaneously. FIG. 5 is a flow diagram depicting a correction method 500 that may be utilized by measurement systems that are capable of acquiring both wafer front and back surfaces for more efficient surface error reduction.

More specifically, as shown in FIG. 5, the method 500 may first acquire phase maps of the front and back surfaces of the wafer and calculate a front surface height map and a back surface height map based on the acquired phase maps in step 502. Subsequently, step 504 may calculate wafer thickness data based on the front and back surface height maps. The wafer thickness data (e.g., expressed using wafer thickness maps and/or thickness variation histograms or the like) may then be utilized in step 506 to identify regions that may be considered the as erroneous/artifact regions.

For example, if a region contains no surface error from phase unwrapping, its corresponding wafer thickness typically has a very narrow variation range and its corresponding thickness variation histogram typically has a very sharp peak centered at approximately 0 nm. However, if a region does contain surface errors, its corresponding thickness variation histogram may present a large spread. A threshold may therefore be defined manually (e.g., according to defined or required thickness variation ranges or limits) and/or systematically (e.g., based on histogram distributions or other statistical parameters) to help identify the regions that have large spread greater than the threshold value. Such regions may be considered the erroneous/artifact regions.

Once the artifact regions have been identified, process steps similar to steps 210-214 (previously described) may be utilized to make corrections to the wafer surface height map. More specifically, step 508 may fit a polynomial of a selected order (e.g., a two-dimensional polynomial) to the front surface height map containing only the artifact-free regions to generate a reference height map; step 510 may calculate the surface height correction values based on the difference between the reference height map and the original surface height map; and step 512 may calculate the final corrected wafer surface height map for the front wafer surface.

It is noted that the abilities to acquire both wafer front and back surface maps may support not only effective surface error correction processes, but also effective generation of phase maps with sparse fringe patterns that are more useful for analysis purposes. More specifically, it is noted that when performing the pattern wafer analysis, it is often required to separate the high frequency pattern components from the relatively low frequency shape components, or to perform certain filtering processes in order to suppress the pattern components in the front surface phase map. However, due to the structures present on the front surface, the front surface is often strongly bowed and has much higher surface slopes than those of bare wafers. Consequently, the phase maps obtained for patterned wafers may have very dense phase fringes, which may increase the cost of the analysis process and decrease its effectiveness.

Figure 6:
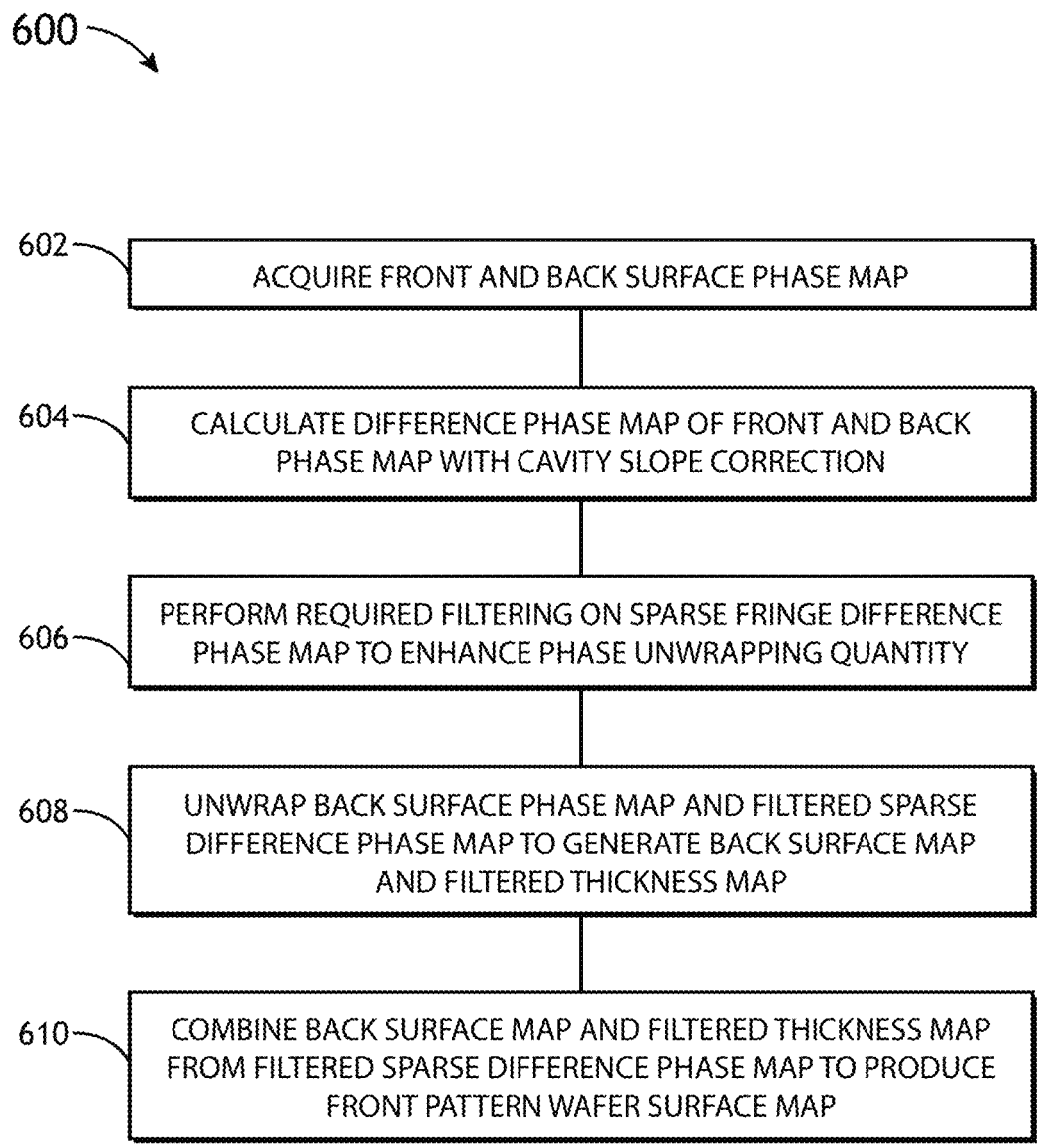
FIG. 6 is a flow diagram depicting an embodiment of a method for reconstruction of a wafer surface map.
Figure 7:
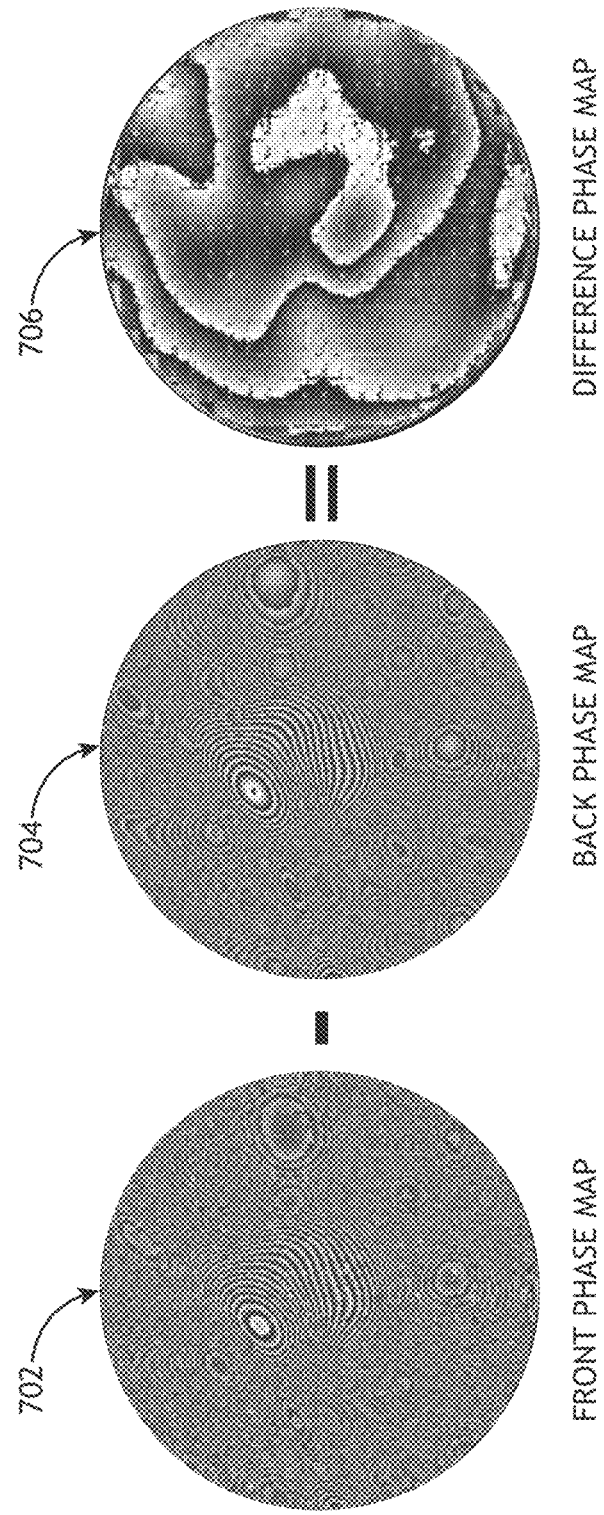
FIG. 7 is an illustration depicting generation of a difference phase map.

FIG. 6 is a flow diagram depicting a method 600 that may be utilized to improve the effectiveness of the phase map analysis. As shown in FIG. 6, the method 600 may first acquire phase maps of the front and back surfaces in step 602. Subsequently, step 604 may calculate the difference of the front and back phase maps. As illustrated in FIG. 7, the difference of the front and back phase maps (702 and 704, respectively) may be referred to as the difference phase map 706, which has sparse fringe patterns that can be more efficiently handled for analysis, processing and/or unwrapping purposes. Unlike phase maps with dense fringes, larger filter kernels can be used for phase maps with sparse fringe patterns to suppress pattern components with long extents and, in many cases, two dimensional filtering approaches, instead of one-dimensional filtering, can be employed to obtain more effective filtering in step 606 for pattern component removal or separation. After the pattern components have been removed from the difference phase map 706, the resulting difference phase map 706 and the back phase map 704 can be unwrapped in step 608 and combined in step 610 to indirectly produce a reconstructed front phase map with pattern components (errors) removed. It is noted that since the back surface usually has much better signal quality (due to the lack of pattern components and film structures) and that the signal quality can be further enhanced by effective filtering, this indirect calculation of the front surface may be able to produce better front surface reconstruction results compared to results obtained by unwrapping the front phase map 702 directly.

Figure 8:
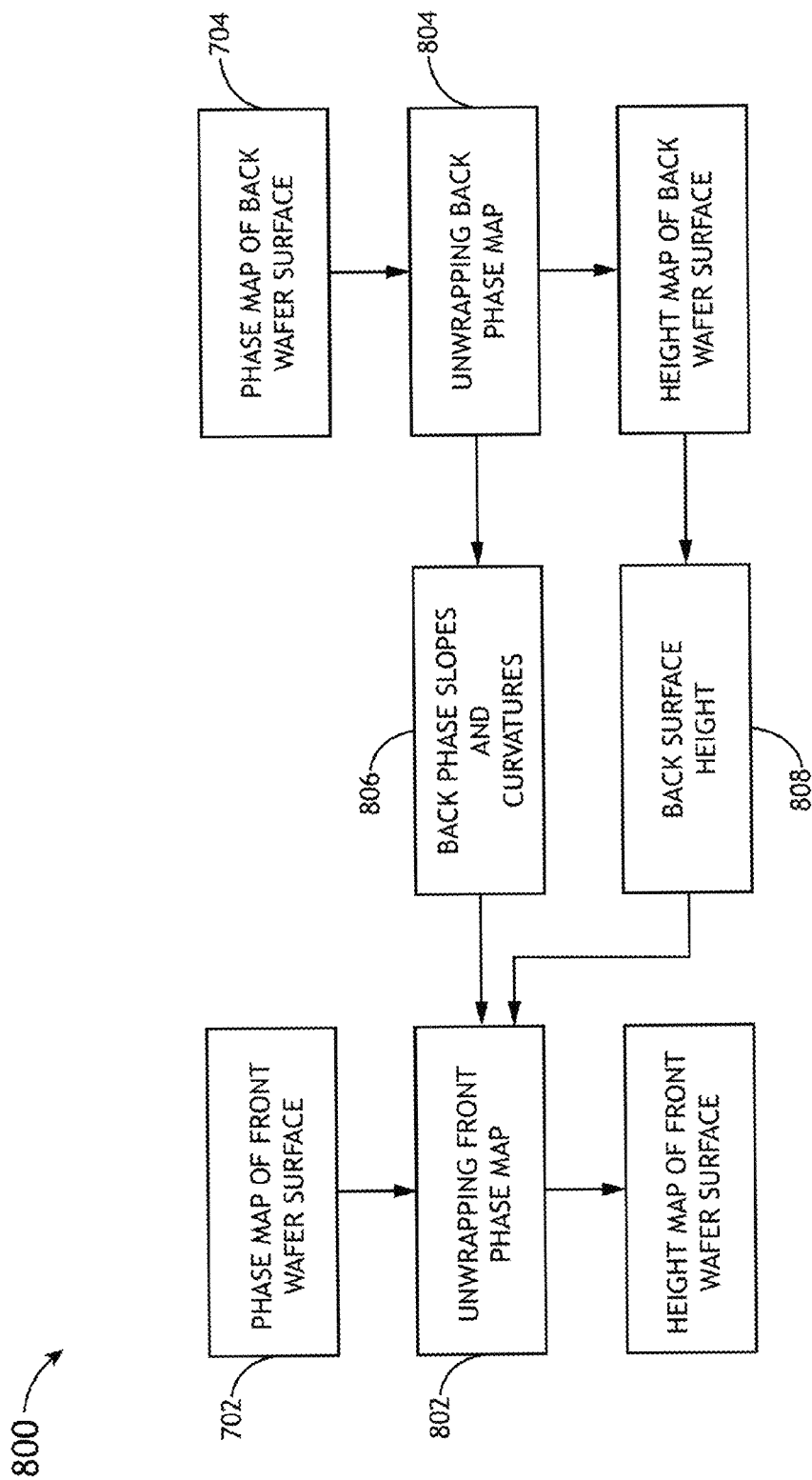
FIG. 8 is a flow diagram depicting an embodiment of a method for unwrapping a front surface phase map with assistance of information obtained from unwrapping a back surface phase map.

It is contemplated that the back phase map 704 may also be utilized to help unwrap the front phase map 702 in certain implementations. For instance, as shown in FIG. 8, the front phase map 702 and the back phase map 704 may be unwrapped in steps 802 and 804, respectively, to obtain the front and back wafer surface height maps. It is noted that since wafers are constructed using solid materials, the front and back wafer surfaces may have similar large scale shapes and, therefore, similar large scale surface slopes. It is also noted that the heights of the front and back surfaces are related by the wafer thickness. These important relations between the front and back wafer surfaces can be utilized to help improve the reconstruction of the front wafer surface in step 802, where the calculated back surface slope and curvature values of both X and Y directions in the back surface unwrapping process may be provided (via step 806) to step 802, which may use the information provided by step 806 to constrain the large scale surface slope values calculated from the front surface phase map.

It is also noted that information regarding the back surface height map may also be fed to step 802 (via step 808). The back surface height map may be taken into consideration in step 802 during the front surface unwrapping process so that the calculated front surface height map will not deviate from the range defined by the back wafer surface height and the specified wafer thickness variation limits. Since the back wafer surfaces of the patterned wafers usually have much better signal quality than the front wafer surface and the back wafer surface can be well reconstructed, the information from the back surface phase and the height maps are very helpful in the effective improvement of the front surface reconstruction by use of this new phase unwrapping method 800.

Figure 9:
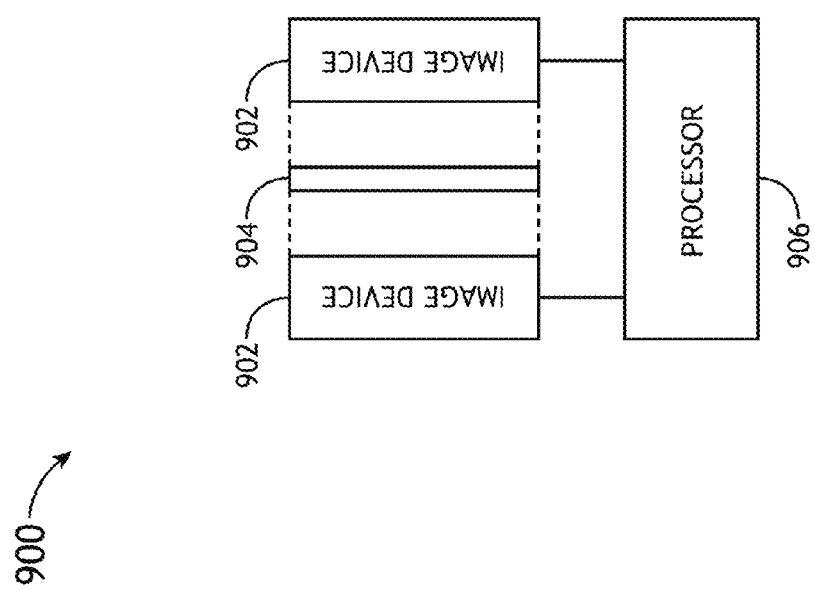
FIG. 9 is a block diagram depicting an embodiment of a wafer measurement system.

Referring now to FIG. 9, a block diagram depicting a wafer metrology tool 900 capable of performing the various correction methods described above is shown. The wafer metrology tool 900 may include one or more imaging devices (e.g., cameras, scanners, microscopes, interferometers or the like) 902 configured to acquire front and back surface image/video frames of a wafer 904.

Data acquired by the imaging device 902 may then be provided to a processor 906 configured to processing the acquired data. The processor 906 may be implemented utilizing any standalone or embedded computing device (e.g., a computer, a processing unit/circuitry or the like). Upon receiving the data from the imaging device 902, the processor 906 may process the received data to reconstruct the wafer surface maps as described above.

It is to be understood that the wafer metrology tool 900 may be utilized to improve performance of various processes related to wafer fabrication. For instance, the wafer metrology tool 900 may be utilized in conjunction with existing techniques to facilitate defect detection processes. In another example, the wafer metrology tool 900 may be used as feed-forward and/or feedback controls for a variety of fabrication processes.

It is contemplated that the advantages provided by the systems and methods in accordance with the present disclosure may be appreciated in various applications. It is contemplated that while some of the examples above referred to certain specific process tools, the systems and methods in accordance with the present disclosure are applicable to other types of process tools, which may also benefit from resolution-enhanced measurements without departing from the spirit and scope of the present disclosure. In addition, it is contemplated that the term wafer used in the present disclosure may include a thin slice of semiconductor material used in the fabrication of integrated circuits and other devices, as well as other thin polished plates such as magnetic disc substrates, gauge blocks and the like.

The methods disclosed may be implemented in various wafer geometry measurement tools as sets of instructions executed by one or more processors, through a single production device, and/or through multiple production devices. Further, it is understood that the specific order or hierarchy of steps in the methods disclosed are examples of exemplary approaches. Based upon design preferences, it is understood that the specific order or hierarchy of steps in the method can be rearranged while remaining within the scope and spirit of the disclosure. The accompanying method claims present elements of the various steps in a sample order, and are not necessarily meant to be limited to the specific order or hierarchy presented.

It is believed that the system and method of the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory.

What is claimed is:

1. A system, comprising:
   at least one imaging device configured to acquire at least one of an image of a front surface of a wafer and at least one image of a back surface of the wafer; and
   at least one processor in communication with the at least one imaging device, the at least one processor configured to:
   calculate at least one of a front surface phase map of the wafer based on the image of the front surface of the wafer and a back surface phase map of the wafer based on the image of the back surface of the wafer;
   calculate at least one of a front surface height map based on the front surface phase map and a back surface height map based on the back surface phase map of the wafer;
   identify at least one artifact region within the front surface height map based on at least one of the front surface height map and the back surface height map;
   generate a reference height map based on the front surface height map with the at least one artifact region excluded;
   calculate a surface height correction value at least partially based on the reference height map, the front surface height map, and the front surface phase map; and
   apply the surface height correction value to obtain an error-corrected front surface height map.

2. The system of claim 1, wherein the at least one processor is configured to identify the at least one artifact region by:
   filtering the front surface height map;
   identifying at least one region within the front surface height map that contains large height variations; and
   performing convex hull analysis of the front surface height map based on the at least one region to identify the at least one artifact region.

3. The system of claim 2, wherein the front surface height map is filtered by high-pass filtering.

4. The system of claim 1, wherein the at least one processor is configured to identify the at least one artifact region by:
   calculating wafer thickness data based on the front surface height map and the back surface height map; and
   identifying the at least one artifact region within the front surface height map based on the wafer thickness data.

5. The system of claim 4, wherein the wafer thickness data includes at least one of: a wafer thickness map and a thickness variation histogram.

6. The system of claim 5, wherein the at least one processor is configured to identify the at least one artifact region by:
   identifying at least one region within the front surface height map that contains a large thickness variation spread as the at least one artifact region.

7. The system of claim 1, wherein the at least one processor is configured to generate the reference height map by:
   fitting a polynomial of a selected order to the front surface height map with the at least one artifact region excluded to generate the reference height map.

8. The system of claim 1, wherein the at least one processor is configured to calculate the surface height correction value by:
   calculating a large scale surface height correction value based on a difference between the reference height map and the front surface height map calculated based on the front surface phase map.

9. The system of claim 8, wherein the large scale surface height correction value is an integer multiple of $\lambda/2$ where $\lambda$ is a wavelength of a laser used to acquire the front surface phase map of the wafer.

10. The system of claim 9, wherein the at least one processor is configured to calculate the surface height correction value by:
calculating a detailed scale surface height correction value for the at least one artifact region excluded from the front surface height map.

11. The system of claim 10, wherein the detailed scale surface height correction value is applied after applying the large scale surface height correction value to further correct the error-corrected front surface height map so that the error-corrected front surface height map corresponds to a phase map that is substantially identical to the front surface phase map of the wafer originally acquired in the acquiring step.

12. The system of claim 1, wherein the at least one processor is further configured to unwrap the front surface phase map by taking into consideration at least one of: the back surface phase map and the back surface height map.

13. The system of claim 1, wherein the at least one processor is further configured to calculate the front surface height map by taking into consideration at least one of: the back surface phase map and the back surface height map.

14. A method, comprising:
acquiring a front surface phase map of a wafer;
calculating a front surface height map based on the front surface phase map;
filtering the front surface height map;
identifying at least one region within the front surface height map that contains large height variations;
performing convex hull analysis of the front surface height map based on the at least one region to identify at least one artifact region;
generating a reference height map based on the front surface height map with the at least one artifact region excluded;
calculating a surface height correction value at least partially based on the reference height map, the front surface height map, and the front surface phase map; and
applying the surface height correction value to obtain an error-corrected front surface height map.

15. The method of claim 14, wherein said filtering the front surface height map further comprises:
filtering the front surface height map using high-pass filtering.

16. The method of claim 14, wherein said identifying at least one region within the front surface height map containing large height variations further comprises:
identifying at least one region within the front surface height map that contains height variations above a surface height variation threshold.

17. The method of claim 14, wherein said generating a reference height map further comprises:
fitting a polynomial of a selected order to the front surface height map with the at least one artifact region excluded to generate the reference height map.

18. The method of claim 14, wherein said calculating a surface height correction value further comprises:
calculating a large scale surface height correction value based on a difference between the reference height map and the front surface height map calculated based on the front surface phase map.

19. The method of claim 18, wherein the large scale surface height correction value is an integer multiple of $\lambda/2$ where $\lambda$ is a wavelength of a laser used to acquire the front surface phase map of the wafer.

20. The method of claim 19, wherein said calculating a surface height correction value further comprises:
calculating a detailed scale surface height correction value for the at least one artifact region excluded from the front surface height map.

21. The method of claim 20, wherein the detailed scale surface height correction value is applied after applying the large scale surface height correction value to further correct the error-corrected front surface height map so that the error-corrected front surface height map corresponds to a phase map that is substantially identical to the front surface phase map of the wafer originally acquired in the acquiring step.

22. A method, comprising:
acquiring a front surface phase map of wafer and a back surface phase map of the wafer;
calculating a front surface height map based on the front surface phase map and a back surface height map based on the back surface phase map of the wafer;
calculating wafer thickness data based on the front surface height map and the back surface height map;
identifying at least one artifact region within the front surface height map based on the wafer thickness data;
generating a reference height map based on the front surface height map with the at least one artifact region excluded;
calculating a surface height correction value at least partially based on the reference height map, the front surface height map, and the front surface phase map; and
applying the surface height correction value to obtain an error-corrected front surface height map.

23. The method of claim 22, wherein the wafer thickness data includes at least one of: a wafer thickness map and a thickness variation histogram.

24. The method of claim 23, wherein said identifying at least one artifact region within the front surface height map further comprises:
identifying at least one region within the front surface height map that contains a large thickness variation spread as the at least one artifact region.

25. The method of claim 22, wherein said generating a reference height map further comprises:
fitting a polynomial of a selected order to the front surface height map with the at least one artifact region excluded to generate the reference height map.

26. The method of claim 22, wherein said calculating a surface height correction value further comprises:
calculating a large scale surface height correction value based on a difference between the reference height map and the front surface height map calculated based on the front surface phase map.

27. The method of claim 26, wherein the large scale surface height correction value is an integer multiple of $\lambda/2$ where $\lambda$ is a wavelength of a laser used to acquire the front surface phase map of the wafer.

28. The method of claim 27, wherein said calculating a surface height correction value further comprises:
calculating a detailed scale surface height correction value for the at least one artifact region excluded from the front surface height map.

29. The method of claim 28, wherein the detailed scale surface height correction value is applied after applying the large scale surface height correction value to further correct the error-corrected front surface height map so that the error-corrected front surface height map corresponds to a phase map that is substantially identical to the front surface phase map of the wafer originally acquired in the acquiring step.

* * * * *